(12) United States Patent
Inamori (10) Patent No.: US 7,814,801 B2
(45) Date of Patent: Oct. 19, 2010

(54) BEND SENSOR (75) Inventor: Dohaku Inamori, Saku (JP)

(73) Assignee: Minebea Co., Ltd., Nagano-ken (JP)

( * ) Notice: Subject to any disclaimer, the term of this patent is extended or adjusted under 35 U.S.C. 154(b) by 105 days.

(21) Appl. No.: 12/285,495

(22) Filed: Oct. 7, 2008

(65) Prior Publication Data
US 2009/0107251 A1  Apr. 30, 2009

(30) Foreign Application Priority Data
Oct. 30, 2007  (JP) .............................. 2007-281786

(51) Int. Cl.
*G01N 3/20*  (2006.01)
*G01L 1/22*  (2006.01)
*G01L 1/04*  (2006.01)

(52) U.S. Cl. ................ 73/849; 73/862.474; 73/862.637

(58) Field of Classification Search .................. 73/849, 73/767, 862.471, 862.474, 862.621, 862.627, 73/862.632, 862.634, 862.637, 862.639, 73/812, 862.451
See application file for complete search history.

(56) References Cited

U.S. PATENT DOCUMENTS

| 5,652,395 | A | * | 7/1997 | Hirano et al. ................. 73/849 |
| 5,799,533 | A | * | 9/1998 | Seki et al. ...................... 73/172 |
| 6,874,378 | B2 | * | 4/2005 | Lautzenhiser et al. .. 73/862.627 |
| 2009/0151478 | A1 | * | 6/2009 | Shimomoto et al. ..... 73/862.626 |

FOREIGN PATENT DOCUMENTS

JP  6-123604  5/1994

* cited by examiner

*Primary Examiner*—Lisa M Caputo
*Assistant Examiner*—Jonathan Dunlap
(74) *Attorney, Agent, or Firm*—Wenderoth, Lind & Ponack, L.L.P.

(57) ABSTRACT

A bend sensor according to one aspect of the present invention is a bend sensor for sensing a bend of a base member in a longitudinal direction comprising: the base member; and a plurality of strain sensitive elements which are disposed at different positions in a width direction on an one side surface of the base member and are disposed at two or more different positions in a thickness direction of the base member.

7 Claims, 5 Drawing Sheets

BEND SENSOR

CROSS-REFERENCE TO RELATED APPLICATION

This application is based upon and claims the benefit of priority from prior Japanese Patent Application No. 2007-281786 filed on Oct. 30, 2007; the entire contents of which are incorporated herein by reference.

BACKGROUND OF THE INVENTION

1. Field of the Invention

The present invention relates to a bend sensor for detecting the degree of bend of an elastic plate.

2. Related Background Art

There has been conventionally a bend sensor for detecting the degree of bend of an elastic plate by detecting dimensional variations generated at an obverse and a reverse of the elastic plate when the elastic plate obtained by mutually sticking, at bottom surfaces thereof, two base members made of a plate-like elastic member having a strain gage or a thick film resistor formed thereon, respectively, is bent.

A general discussion will be first conducted on the principle of a bend sensor.

Figure 8:
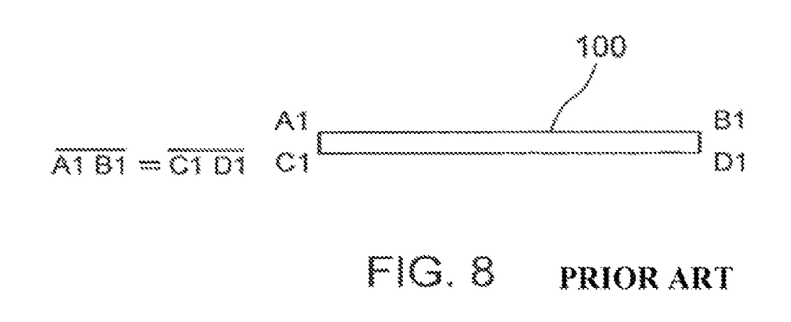
FIG. 8 is a side view schematically showing an elastic plate constituting a bend sensor.
Figure 9:
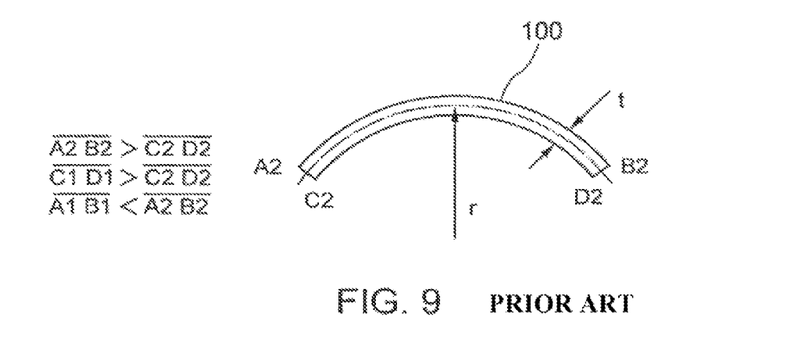
FIG. 9 is a side view showing a state in which the elastic plate is bent.

FIG. 8 is a side view schematically showing an elastic plate constituting a bend sensor. FIG. 9 is a side view showing a state in which the elastic plate is bent.

As shown in FIG. 8, it is assumed that each of an obverse side A1B1 and a reverse side C1D1 of an elastic plate 100 has a length L1 in an initial state.

An external force is exerted on the elastic plate 100, which is then curved at a radius r of curvature on a neutral line of a sensor, as shown in FIG. 9. At this time, it is assumed that an arc A2B2 of the curved side A1B1 has a length L2 (>L1) while an arc C2D2 of the curved side C1D1 has a length L3 (<L1).

Here, a strain $\epsilon_{AB}$ at the obverse of the elastic plate caused by the bend is expressed by the following equation:

$$\epsilon_{AB} = \Delta L2/L1 = (L2-L1)/L1 \qquad (1)$$

The right side of the equation is expressed by using the radius r of curvature on the neutral line, as follows:

$$\begin{aligned}\varepsilon_{AB} &= (L2 - L1)/L1 \\ &= [2\pi\{(t/2) + r\} - 2\pi r]/2\pi r \\ &= \pi t / 2\pi r\end{aligned} \qquad (2)$$

Similarly, a strain $\epsilon_{CD}$ at the reverse of the elastic plate caused by the bend is expressed by the following equation:

$$\epsilon_{CD} = \Delta L3/L1 = (L3-L1)/L1 \qquad (3)$$

The right side of the equation is expressed by using the radius r of curvature on the neutral line, as follows:

$$\begin{aligned}\varepsilon_{CD} &= (L3 - L1)/L1 \\ &= [2\pi\{-(t/2) + r\} - 2\pi r]/2\pi r \\ &= -\pi t / 2\pi r \\ &= -\varepsilon_{AB}\end{aligned} \qquad (4)$$

As a consequence, in the case where a 4-active bridge circuit having two strain gages disposed at each of the obverse and reverse of the elastic plate, that is, four strain gages in total is configured, an output of one active bridge circuit corresponding to one strain gage is expressed by the following equation:

$$e1 = (E/4) K \epsilon_{AB}$$

where E represents an applied voltage of the entire 4-active bridge circuit, and further, K indicates a gage coefficient thereof. In consideration of a polarity of the voltage, the output of the 4-active bridge circuit is expressed by the following equation:

$$e = 4 \times e1 = E K \epsilon_{AB}$$

As is obvious from the equations (2) and (4), as the radius r of bend curvature, or the radius r of curvature of the bend sensor becomes smaller, a magnitude (i.e., an absolute value) of each of the strains $\epsilon_{AB}$ and $\epsilon_{CD}$ becomes greater. And as a thickness t of the elastic plate becomes greater, the magnitude of each of the strains $\epsilon_{AB}$ and $\epsilon_{CD}$ becomes greater.

Figure 10:
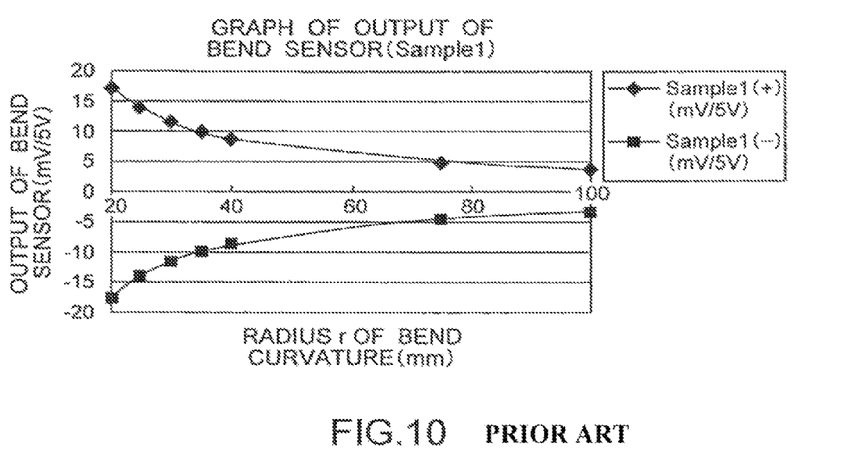
FIG. 10 is a graph illustrating the relationship between the radius r of curvature of the bend sensor and an output of the bend sensor.

FIG. 10 is a graph illustrating the relationship between the radius r of curvature of the bend sensor and an output of the bend sensor.

As also illustrated in the graph of FIG. 10, as the radius r of bend curvature, or the radius r of curvature of the bend sensor becomes smaller, the magnitude (absolute value) of each of the strains $\epsilon_{AB}$ and $\epsilon_{CD}$ becomes greater.

One example of the conventional bend sensor in accordance with the above-described principle has been proposed and known by a bend sensor constituting a Wheatstone bridge circuit, in which elastic plates obtained by mutually sticking bottom surfaces of two base members made of a plate-like elastic member having a resistor variable in resistance in response to bend, that is, a strain, formed thereon are connected at the resistors thereof to each other. See, for example, Japanese Patent Laid-Open Publication No. 6-123604A.

However, in the conventional bend sensor obtained by mutually sticking, at bottom surfaces thereof, the two base members made of the plate-like elastic member having the strain gage or the thick film resistor formed thereon, respectively, a through hole need be bored in the elastic plate having the two base members stuck to each other, and then, strain sensitive elements need be connected to each other in order to constitute a bridge circuit by connecting the strain sensitive elements disposed at an obverse and a reverse to each other, thereby raising a problem of the necessity of a fabrication process therefor.

Figure 11:
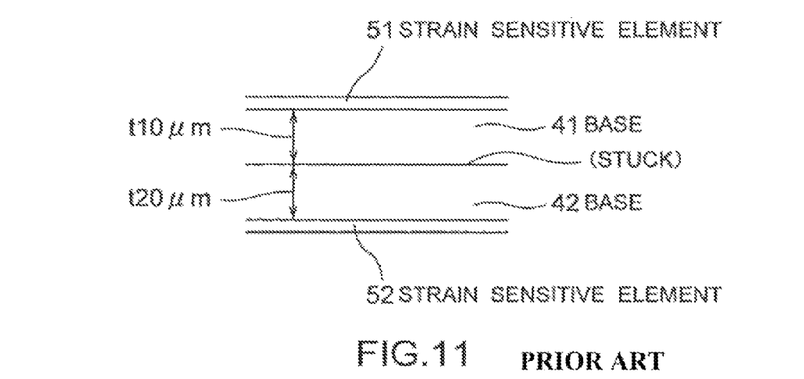
FIG. 11 is a side view showing a part of the conventional bend sensor, in which two base members, each having a strain sensitive element formed at an obverse thereof, are stuck to each other.

FIG. 11 is a side view showing a part of the conventional bend sensor, in which two base members, each having a strain sensitive element formed at an obverse thereof, are stuck to each other.

As shown in FIG. 11, the conventional bend sensor is constituted by mutually sticking a base member 41 having a strain sensitive element 51 formed thereon and another base member 42 having another strain sensitive element 52 formed thereon.

Therefore, in order to constitute a bridge circuit by connecting the strain sensitive elements 51 and 52 to each other, through holes need be bored in the base members 41 and 42 stuck to each other, and then, the strain sensitive elements 51 and 52 need be connected to each other. Accordingly, a fabrication process is required therefor.

Moreover, in sticking the base members 41 and 42 to each other, the obverse and reverse strain sensitive elements 51 and 52 need be accurately aligned each other, thereby requiring a time for a sticking process and degrading a yield.

Additionally, the conventional bend sensor has the structure in which the two base members 41 and 42 are stuck to each other, and therefore, the entire thickness of the elastic plate except the strain sensitive elements 51 and 52 becomes as large as t10+t20, wherein the thicknesses of the base members 41 and 42 are designated by t10 and t20, respectively. For example, although the base members 41 and 42, each having a thickness of 25 µm, can be formed, the entire thickness of the elastic plate except the strain sensitive elements 51 and 52 becomes twice, that is, as large as 50 µm by sticking the base members 41 and 42 to each other.

When the elastic plate receives bend at a small radius r of bend curvature, that is, when a large external force is exerted on the bend sensor in the case that the elastic plate constituting the bend sensor is thick, a strain at the strain sensitive elements 51 and 52 becomes excessive, thereby exerting a harmful effect of a shortage of a fatigue lifetime. For example, when bend at a radius r of bend curvature of 20 mm is applied to the elastic plate having a thickness of 50 µm, a strain at the strain sensitive elements 51 and 52 becomes about 2500 µε, so that only several tens of thousands of bending times can be expected in regard to a fatigue lifetime. According to usage, the fatigue lifetime of the bend sensor is desired to be a million of bending times.

SUMMARY OF THE INVENTION

An object of the present invention is to provide a bend sensor which can be fabricated in a simple fabrication process without any necessity of sticking of base members, boring of a through hole in an elastic plate and wiring connection via the through hole, has a thin elastic plate, and has a remarkably prolonged fatigue lifetime.

According to one aspect of the present invention, there is provided a bend sensor for sensing a bend of a base member in a longitudinal direction comprising: the base member; and a plurality of strain sensitive elements which are disposed at different positions in a width direction on an one side surface of the base member and are disposed at two or more different positions in a thickness direction of the base member.

According to another aspect of the present invention, there is provided a bend sensor comprising:

a base member having M projections and depressions in total (here, M is an odd number of 3 or more) formed alternately in a stripe manner in a longitudinal direction and symmetrically with respect to a center line parallel to a thickness direction in a cross section in a direction perpendicular to the longitudinal direction, in which respective obverses and reverses of the projections and the depressions correspond to each other in a one-to-one manner;

N strain sensitive elements (here, N=M−2) formed on N projections or depressions on the same side except projections or depressions located at both ends of the M projections and depressions in the base member, and bisected strain sensitive elements electrically connected to each other and formed on the projections or the depressions located at both ends of the M projections and depressions on the same side as the N strain sensitive elements, the bisected strain sensitive elements being equivalent to one of the N strain sensitive elements;

core members formed to be fitted to the depressions on the reverse side of the projections having the strain sensitive elements formed thereon respectively and formed to be fitted to the depressions having the strain sensitive elements formed thereon respectively;

a connection wiring for interconnecting the strain sensitive elements so as to constitute a bridge circuit on the same side of the base member; and a cover member formed to cover the strain sensitive elements formed on the projections in the base member.

Each of the strain sensitive elements may be a strain gage resistance element.

The odd numbers M and N are 5 and 3, respectively, in the case where the bridge circuit is a 4-active bridge circuit, and the odd numbers M and N are 3 and 1, respectively, in the case where the bridge circuit is a 2-active bridge circuit.

The base member and the cover member may be made of an organic molecular film including a polyimide film, or made of a resin film.

Each of the strain sensitive elements and the connection wiring may be formed by using photolithography.

With the above-described configuration, the bend sensor in one embodiment according to the present invention can be fabricated in the simple fabrication process without any necessity of the sticking of the base members, the boring of the through hole in the elastic plate and the wiring connection via the through hole, thus producing effects of the thinness of the elastic plate and the remarkably long fatigue lifetime.

DETAILED DESCRIPTION OF THE EMBODIMENTS

A bend sensor according to the present invention is a bend sensor for sensing a bend of a base member in a longitudinal direction comprising a plurality of strain sensitive elements which are disposed at different positions in a width direction on an one side surface of the base member and are disposed at two or more different positions in a thickness direction of the base member.

Hereinafter, a description will be given in detail of a bend sensor in one embodiment according to the present invention in reference to the attached drawings.

Figure 1:
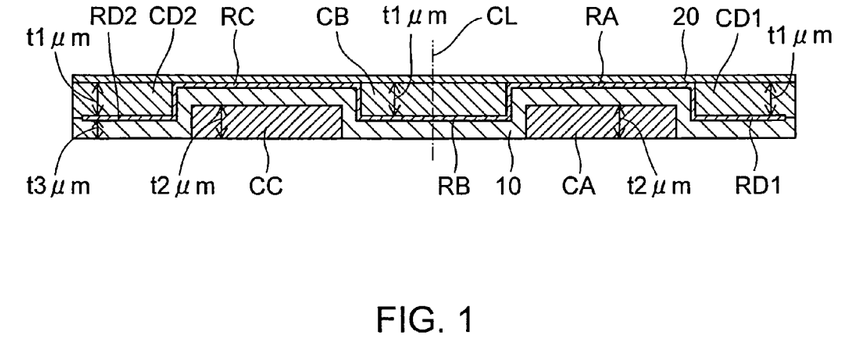
FIG. 1 is a cross-sectional view showing the structure of a bend sensor in one embodiment according to the present invention.
Figure 2:
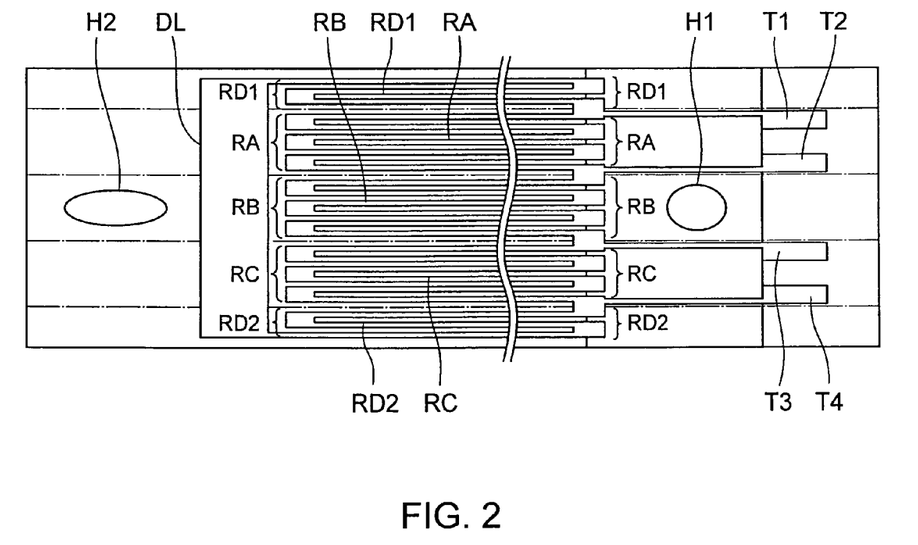
FIG. 2 is a plan view showing the bend sensor in the one embodiment according to the present invention.

FIG. 1 is a cross-sectional view showing the structure of a bend sensor in one embodiment according to the present invention. FIG. 2 is a plan view showing the bend sensor in the one embodiment according to the present invention.

The bend sensor in the one embodiment according to the present invention includes: a base member 10 having M projections and depressions in total (here, M is an odd number of 3 or more, for example, 5 in FIG. 1) formed alternately in a stripe manner in a longitudinal direction and symmetrically with respect to a center line CL parallel to a thickness direction in a cross section in a direction perpendicular to the longitudinal direction, in which respective obverses and reverses of the projections and the depressions correspond to each other in a one-to-one manner so that the reverse of the projection serves as the depression; N strain sensitive elements RA, RB and RC (here, N=M−2, for example, 3 in FIG. 1) formed on N projections or depressions on the same side except projections or depressions located at both ends of the M projections and depressions in the base member 10, and bisected strain sensitive elements RD1 and RD2 electrically connected to each other and formed on the projections or the depressions located at both ends of the M projections and depressions on the same side as the N strain sensitive elements RA, RB and RC, the bisected strain sensitive elements RD1 and RD2 being equivalent to one of the N strain sensitive elements RA, RB and RC; core members CA and CC formed in such a manner as to be fitted to the depressions on the reverse side of the projections having the strain sensitive elements RA and RC formed thereon respectively and core members CB, CD1 and CD2 formed in such a manner as to be fitted to the depressions having the strain sensitive elements RB, RD1 and RD2 formed thereon respectively; a connection wiring for interconnecting the strain sensitive elements RA, RB, RC, RD1 and RD2 so as to constitute a bridge circuit on the same side of the base member 10; and a cover member 20 formed in such a manner as to cover the strain sensitive elements RA and RC formed on the projections in the base member 10.

As shown in FIG. 2, the projections and the depressions in the base member 10 and the strain sensitive elements RA, RB, RC, RD1 and RD2 are formed in the stripe manner along the longitudinal direction of the bend sensor, as viewed from the top.

The bisected strain sensitive elements RD1 and RD2 are electrically connected to each other via a connection wiring DL.

Outputting terminals T1, T2, T3 and T4 are drawn from the bridge circuit.

The strain sensitive elements RA, RB, RC, RD1 and RD2 herein are strain gage resistance elements.

The bend sensor according to the present invention is such configured that the bisected strain sensitive elements RD1 and RD2 are located on both sides of the odd N strain sensitive elements RA, RB and RC symmetrically with respect to the center line in the longitudinal direction for the purpose of elimination of an erroneous operation caused by a torsion or the like.

The base member 10 and the cover member 20 are disposed over the entire length in the longitudinal direction.

When the bend sensors are bonded at the obverse or reverse thereof in use, free deformation of the bend sensor shown in FIG. 9 is prevented, and therefore, a satisfactory output cannot be obtained. In other words, the bend sensors need be bonded at neither obverse nor reverse thereof in order to obtain an output of a high accuracy, and then, need be mounted in such a manner that a strain becomes zero at a center in a thickness direction of the bend sensor and strain polarities at the obverse and the reverse becomes contrary to each other in accordance with the principle shown in FIGS. 8 and 9. In FIG. 2, a circular opening H1 for fixing the bend sensor is formed in the vicinity of one end on the center line in the longitudinal direction whereas an oblong or elliptic opening H2 for fixing the bend sensor while enabling the bend sensor to perform a bending operation is formed in the vicinity of the other end. Here, the openings at both ends are not always needed. For example, a pocket or the like is disposed at an object, and then, the bend sensor is directly disposed by inserting it into the pocket, thereby eliminating the openings H1 and H2.

The odd numbers M and N are 5 and 3, respectively, in the case where the bridge circuit is a 4-active bridge circuit. Otherwise, M and N are 3 and 1, respectively, in the case where the bridge circuit is a 2-active bridge circuit.

Figure 3:
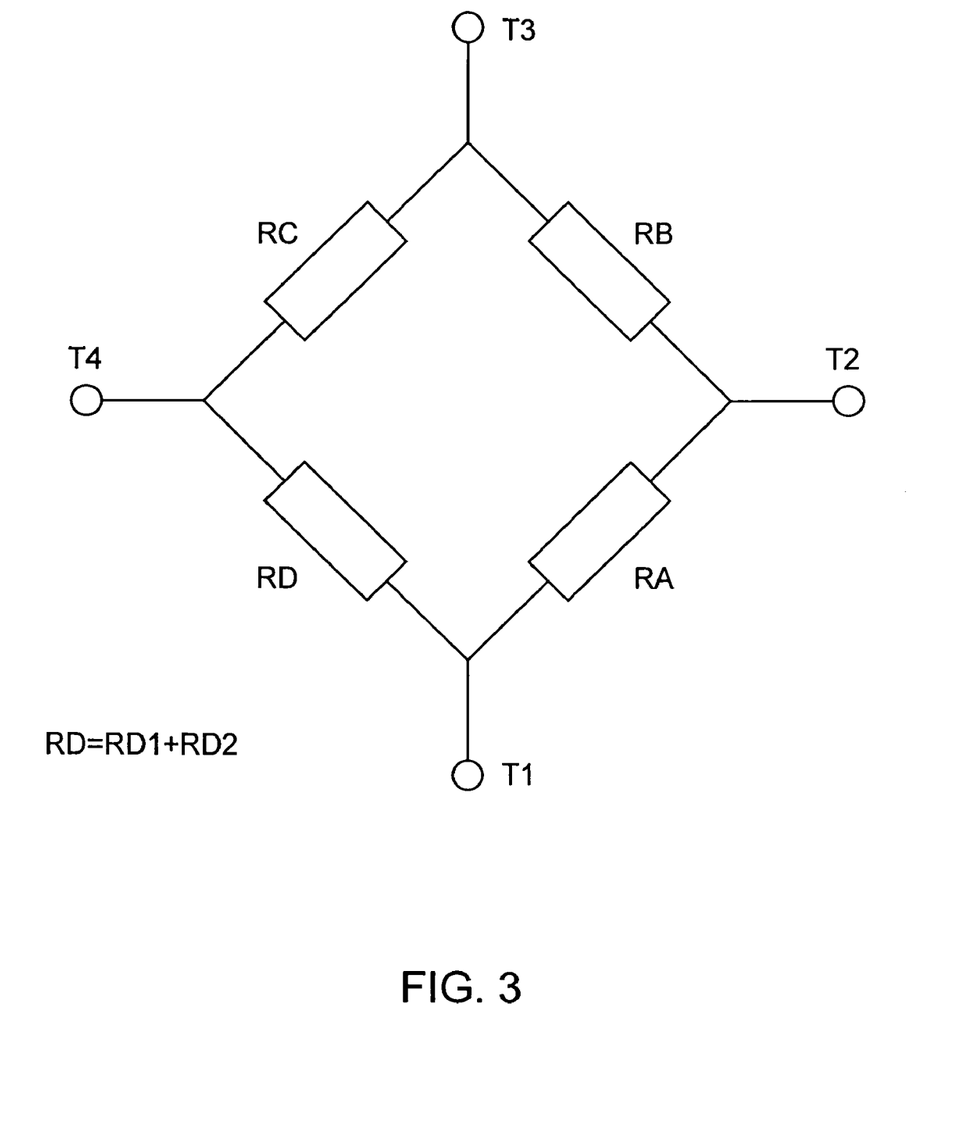
FIG. 3 is a circuit diagram illustrating the bridge circuit constituted of the strain sensitive elements provided in the bend sensor in the one embodiment according to the present invention.

FIG. 3 is a circuit diagram illustrating the bridge circuit constituted of the strain sensitive elements provided in the bend sensor in the one embodiment according to the present invention.

Incidentally, in FIG. 3, the bisected strain sensitive elements RD1 and RD2 electrically connected to each other are unified into one strain sensitive elements RD.

As illustrated in FIG. 3, the series connected strain sensitive elements RA and RB and the series connected strain sensitive elements RC and RD are connected in parallel to each other between the terminals T1 and T3, and further, a connection node between the strain sensitive element RA and the strain sensitive element RB serves as the terminal T2 whereas a connection node between the strain sensitive element RD and the strain sensitive element RC serves as the terminal T4, thus constituting the bridge circuit.

In the bridge circuit, a first output is taken from the terminals T1 and T3, and further, a second output is taken from the terminals T2 and T4. As a consequence, the bridge circuit can function as the 4-active bridge circuit.

Though the above described bend sensor in the one embodiment according to the present invention comprises various limited constituents to achieve functions as a high-accuracy bend sensor, all of those limited constituents are not essential in the bend sensor according to the present invention.

In the above described bend sensor in the one embodiment according to the present invention, the base member 10 has a symmetrical shape with respect to a center line CL parallel to the thickness direction in a cross section in a direction perpendicular to the longitudinal direction. However, the base member comprised in the bend sensor according to the present invention need not necessarily have such the symmetrical shape, when it is not necessary to consider a torsional force severely.

Furthermore, the base member comprised in the bend sensor according to the present invention need not necessarily have projections and depressions in such manner that respective obverses and reverses of the projections and the depressions correspond to each other in a one-to-one manner so that the reverse of the projection serves as the depression. For example, such configuration may be possible in which a base member having varied thickness in a width direction to form the projections and the depressions on obverse is employed without core members, strain sensitive elements is formed on the projections and the depressions, and a cover member having projections and depressions so as to fit with the projections and the depressions of the base member is attached to the base member.

Moreover, the above described bend sensor of the one embodiment according to the present invention has a configuration in which it comprises N strain sensitive elements (N=M−2) and two bisected strain sensitive elements formed on the projections or the depressions located at both ends and being equivalent to one of the N strain sensitive elements. However, the bend sensor according to the present invention need not necessarily have such configuration. For example, when symmetricalness in the width direction is not necessary, two bisected strain sensitive elements need not be employed and an even number of strain sensitive elements may be employed. Even in the case that the bend sensor is to have symmetric configuration, two bisected strain sensitive elements at both ends need not be connected to each other to be equivalent to one of the N strain sensitive elements. For example, dummy elements may be arranged at both ends and the center position, seven elements including three dummy elements in total may be arranged and 4-active bridge circuit may be constituted of four strain sensitive elements other than three dummy elements. Alternatively, five elements including three dummy elements in total may be arranged and 2-active bridge circuit may be constituted of two strain sensitive elements other than three dummy elements.

Furthermore, the cover member need not be comprised as a essential constituent of the present invention. Various materials may be employed as a material of the cover member, and it need not necessarily be a solid member, but, for example, a painting may be employed as the cover member.

Figure 4:
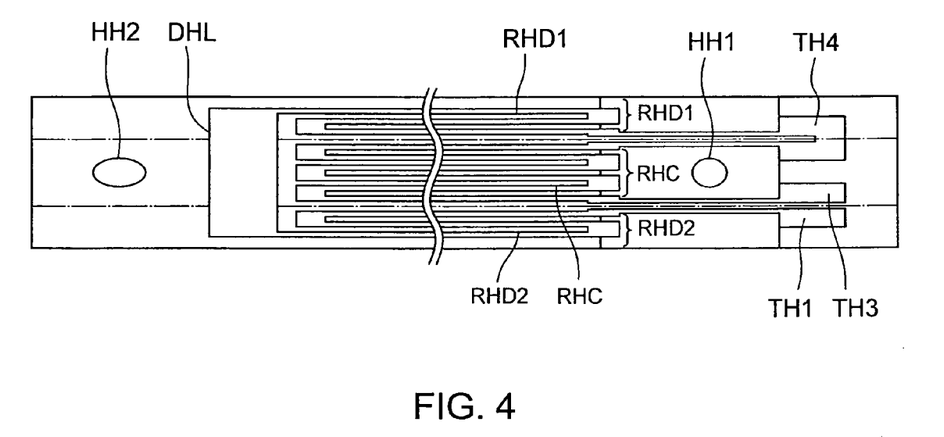
FIG. 4 is a plan view of the bend sensor in another embodiment according to the present invention.

FIG. 4 is a plan view of the bend sensor in another embodiment according to the present invention.

The bend sensor in another embodiment according to the present invention shown in FIG. 4 comprises: a base member 10; a center strain sensitive element RHC arranged on the base member 10; and bisected strain sensitive elements RHD1 and RHD2 bisected to both sides of the center strain sensitive element RHC and arranged on the base member 10. The base member 10 has a shape comprising projections and depressions as well as the base member 10 of the bend sensor in the one embodiment according to the present invention shown in FIGS. 1 and 2. For example, the center strain sensitive element RHC may be arranged on the projections of the base member 10, and the bisected strain sensitive elements RHD1 and RHD2 may be arranged on the depressions of the base member 10. Moreover, core members may be arranged on the bisected strain sensitive elements RHD1 and RHD2 respectively, and a core member may be arranged on the depression of the base member 10, which is the reverse of the projection on which the center strain sensitive element RHC is arranged. Furthermore, the bend sensor in another embodiment according to the present invention may be comprise a cover member 20 formed to cover the center strain sensitive element RHC arranged on the projection of the base member 10.

Comparing with the bend sensor in the one embodiment according to the present invention shown in FIGS. 1 and 2, the bend sensor in another embodiment according to the present invention shown in FIG. 4 has a configuration in which parts of the configuration including the strain sensitive elements RA and RB are omitted, and a configuration of peripheral wirings is partly different as a result of reducing the number of the strain sensitive elements.

Figure 5:
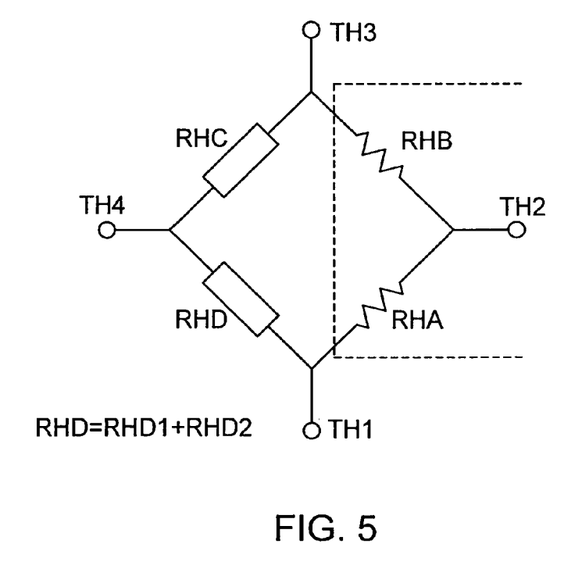
FIG. 5 is a circuit diagram of the bridge circuit constituted of the strain sensitive elements provided in the bend sensor in the another embodiment according to the present invention.

FIG. 5 is a circuit diagram of the bridge circuit partly configured with the strain sensitive elements provided in the bend sensor in the another embodiment according to the present invention.

Incidentally, in FIG. 5, the bisected strain sensitive elements RHD1 and RHD2 electrically connected to each other are unified into one strain sensitive elements RHD.

As illustrated in FIG. 5, the strain sensitive elements RHD and RHC are connected in series between the terminals TH1 and TH3, a connection node between the strain sensitive element RHD and the strain sensitive element RHC serves as the terminal TH4, external resistive elements RHA and RHB are connected in series between the terminals TH1 and TH3, and a connection node between the external resistive elements RHA and RHB serves as the terminal TH2, thus constituting the bridge circuit.

The external resistive elements RHA and RHB are fixed resistor, which are arranged at outside of the bend sensor, for example, on the amplifier substrate. By drawing out a first output from the terminals TH1 and TH3 of the bridge circuit and a second output from terminals TH2 and TH4, the bridge circuit can function as the 2-active bridge circuit.

When the 2-active bridge circuit is configured with the center strain sensitive element RHC, the bisected strain sensitive elements RHD1 and RHD2, and the fixed resistive elements RHA and RHB, all of the elements need not be arranged on the base member of the bend sensor. For example, the fixed resistive elements RHA and RHB may be arranged on the amplifier substrate at outside of the bend sensor.

However, with regard to the elements arranged on the base member of the bend sensor, all of the elements have to be arranged on the surface of the same side of the base member respectively in order to make it unnecessary to form a through hole in the base member for interconnecting each of the elements with each other.

Next, explanation will be made on a fabrication process of the bend sensor in the one embodiment according to the present invention.

Figure 6:
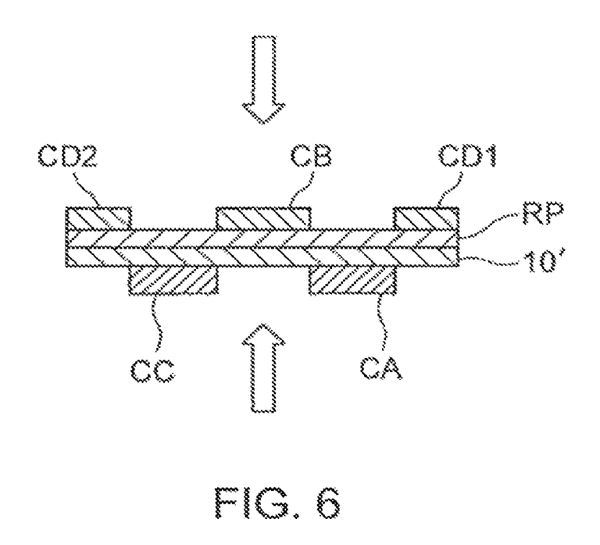
FIG. 6 is a cross-sectional view showing a first fabrication process of the bend sensor in the one embodiment according to the present invention.
Figure 7:
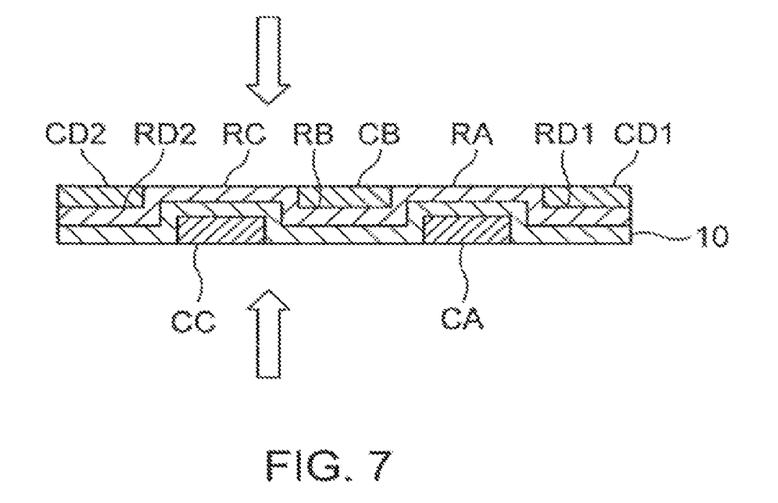
FIG. 7 is a cross-sectional view showing a second fabrication process of the bend sensor in the one embodiment according to the present invention.

FIG. 6 is a cross-sectional view showing a first fabrication process of the bend sensor in the one embodiment according to the present invention, and FIG. 7 is a cross-sectional view showing a second fabrication process of the bend sensor in the one embodiment according to the present invention.

First of all, the strain sensitive elements RA, RB, RC, RD1 and RD2 serving as the strain gage resistance elements, the connection wiring, and the terminals T1, T2, T3 and T4 are formed as a layer RP on a flat base member 10' by patterning with photolithography, as shown in FIG. 6.

And then, the core members CB, CD1 and CD2 are securely bonded in regions to be the depressions in the base member 10' on which the depressions and the projections are to be alternately formed, that is, in regions in which the center strain sensitive element RB and the strain sensitive elements RD1 and RD2 in the odd number counted from the center are formed herein. On the other hand, the core members CA and CC are securely bonded at the reverses in regions to be the projections in the base member 10', that is, at the reverses in regions in which the strain sensitive elements RA and RC in the even number counted from the center are formed herein.

Thereafter, the strain sensitive elements RA, RB, RC, RD1 and RD2 and the base member 10 are machined by vertically pressurizing so that they have a shape in which the depressions and the projections are alternately arranged with the core members CB, CD1 and CD2 at the obverse and the core members CA and CC at the reverse, and further, the core members CB, CD1 and CD2 are fitted into the depressions at the obverse and the core members CA and CC are fitted into the depressions at the reverse, as shown in FIG. 7. In this way, the bend sensor is machined into a flat plate shape as a whole. In pressurizing, heating may be carried out, as required.

Finally, the bend sensor, shown in FIG. 1, in the one embodiment according to the present invention is completed by disposing the cover member 20 covering the strain sensitive elements RA and RC formed in the regions corresponding to the projections in the base member 10.

Here, the base member 10 and the cover member 20 are made of an organic molecular film including a polyimide film or a resin film.

All of the strain sensitive elements are formed on the same side of the base member 10 in the bend sensor in the one embodiment according to the present invention, and therefore, the bend sensor can be fabricated in the simple fabrication process without boring any through hole in the base member 10 as the elastic plate and requiring any wiring connection via the through hole.

Naturally, a process for precisely positioning and sticking the two base members to each other becomes unnecessary, and a material cost can be reduced.

Additionally, assuming that each of thicknesses t1 and t2 of the core members is set to, for example, 50 μm and a thickness t3 of the base member 10 is set to, for example, 25 μm, respectively in FIG. 1, both of dimensions in the thickness direction becomes 25 μm in a step between a center position in the thickness direction of the core members CB, CD1 and CD2 at upper position and the strain sensitive elements RA and RC formed at the projections at highest positions and in a step between the above-mentioned center position and the strain sensitive elements RB, RD1 and RD2 formed at the depressions at lowest positions, thus halving a dimension in the thickness direction of 50 μm between the base members sticking position and the strain sensitive elements at the obverse and a dimension in the thickness direction of 50 μm between the base members sticking position and the strain sensitive elements at the reverse in the conventional bend sensor in the case that both of thicknesses of the two base members thereof are 50 μm, so as to achieve the thin bend sensor having a remarkably prolonged fatigue lifetime. The thickness of each of the strain sensitive elements and the connection wiring is normally from about 4 μm to about 5 μm.

Since the thicknesses t1 and t2 of the core members can be readily adjusted, the effective thickness of the bend sensor also can be readily adjusted.

Assuming that the thicknesses t1 and t2 of the core members are set to, for example, 25 μm, both of dimensions in the thickness direction becomes 12.5 μm in a step between a center position in the thickness direction of the core members CB, CD1 and CD2 at upper position and the strain sensitive elements RA and RC formed at the projections at highest positions and in a step between the above-mentioned center position and the strain sensitive elements RB, RD1 and RD2 formed at the depressions at lowest positions so as to achieve the thinner bend sensor having a more remarkably prolonged fatigue lifetime. Also in this case, a dimension in the thickness direction of 25 μm between the base members sticking position and the strain sensitive elements at the obverse and a dimension in the thickness direction of 25 μm between the base members sticking position and the strain sensitive elements at the reverse in the conventional bend sensor in the case that both of thicknesses of the two base members thereof are 25 μm can be halved.

The effective thickness of the bend sensor may be determined in consideration of a balance of an appropriate radius r of bend curvature and output characteristics.

A resistance balance of the bridge circuit constituted of the strain sensitive elements RA, RB, RC, RD1 and RD2 may be adjusted in advance after the photolithography.

Moreover, the strain sensitive elements RA, RB, RC, RD1 and RD2 are made of the same material and portions very proximate to each other, and therefore, temperature characteristics are very similar to each other, thus suppressing an output error caused by a change in temperature to a very low level.

What is claimed is:

1. A bend sensor comprising:
   a base member having M projections and depressions in total (here, M is an odd number of 3 or more) formed alternately in a stripe manner in a longitudinal direction and symmetrically with respect to a center line parallel to a thickness direction in a cross section in a direction perpendicular to the longitudinal direction, in which respective obverses and reverses of the projections and the depressions correspond to each other in a one-to-one manner;
   N strain sensitive elements (here, N=M−2) formed on N projections or depressions on the same side except projections or depressions located at both ends of the M projections and depressions in the base member, and bisected strain sensitive elements electrically connected to each other and formed on the projections or the depressions located at both ends of the M projections and depressions on the same side as the N strain sensitive elements, the bisected strain sensitive elements being equivalent to one of the N strain sensitive elements;
   core members formed to be fitted to the depressions on the reverse side of the projections having the strain sensitive elements formed thereon respectively and formed to be fitted to the depressions having the strain sensitive elements formed thereon respectively;
   a connection wiring for interconnecting the strain sensitive elements so as to constitute a bridge circuit on the same side of the base member; and
   a cover member formed to cover the strain sensitive elements formed on the projections in the base member.

2. The bend sensor according to claim 1, wherein each of the strain sensitive elements is a strain gage resistance element.

3. The bend sensor according to claim 1, wherein the odd numbers M and N are 5 and 3, respectively, in the case where the bridge circuit is a 4-active bridge circuit.

4. The bend sensor according to claim 1, wherein the odd numbers M and N are 3 and 1, respectively, in the case where the bridge circuit is a 2-active bridge circuit.

5. The bend sensor according to claim 1, wherein the base member and the cover member are made of an organic molecular film including a polyimide film.

6. The bend sensor according to claim 1, wherein the base member and the cover member are made of a resin film.

7. The bend sensor according to claim 1, wherein each of the strain sensitive elements and the connection wiring are formed by using photolithography.

* * * * *